United States Patent
McEwen et al.

(10) Patent No.: US 8,083,763 B2
(45) Date of Patent: Dec. 27, 2011

(54) APPARATUS AND METHOD FOR ESTIMATING LEAKAGE IN A SURGICAL TOURNIQUET SYSTEM

(75) Inventors: James A. McEwen, Vancouver (CA); Michael Jameson, North Vancouver (CA); Michael A. Gebert, New Westminister (CA); William K. W. Cheung, Vancouver (CA)

(73) Assignee: Western Clinical Engineering Ltd., Vancouver ( * ) Notice: Subject to any disclaimer, the term of this patent is extended or adjusted under 35 U.S.C. 154(b) by 379 days.

(21) Appl. No.: 12/368,789

(22) Filed: Feb. 10, 2009

(65) Prior Publication Data

US 2010/0204726 A1   Aug. 12, 2010

(51) Int. Cl.
*A61B 17/135* (2006.01)
(52) U.S. Cl. .............................. 606/202; 73/40; 606/203
(58) Field of Classification Search ....... 73/40; 606/202
See application file for complete search history.

(56) References Cited

U.S. PATENT DOCUMENTS

| | | | |
|---|---|---|---|
| 3,239,257 A | 3/1966 | White | |
| 4,321,929 A | 3/1982 | Lemelson | |
| 4,469,099 A | 9/1984 | McEwen | |
| 4,479,494 A | 10/1984 | McEwen | |
| 4,548,198 A | 10/1985 | Manes | |
| 4,605,010 A | 8/1986 | McEwen | |
| 4,635,635 A | 1/1987 | Robinette-Lehman | |
| 4,671,290 A | 6/1987 | Miller | |
| 4,869,265 A | 9/1989 | McEwen | |
| 5,048,536 A | 9/1991 | McEwen | |
| 5,181,522 A | 1/1993 | McEwen | |
| 5,254,087 A | 10/1993 | McEwen | |
| 5,312,431 A | 5/1994 | McEwen | |
| 5,439,477 A | 8/1995 | McEwen | |
| 5,454,831 A | 10/1995 | McEwen | |
| 5,556,415 A | 9/1996 | McEwen | |
| 5,569,304 A | 10/1996 | Ulrich | |
| 5,578,055 A | 11/1996 | McEwen | |
| 5,584,853 A | 12/1996 | McEwen | |
| 5,607,447 A | 3/1997 | McEwen | |
| 5,649,954 A | 7/1997 | McEwen | |
| 5,681,339 A | 10/1997 | McEwen | |
| 5,741,295 A | 4/1998 | McEwen | |
| 5,855,589 A | 1/1999 | McEwen | |
| 5,911,735 A | 6/1999 | McEwen | |
| 5,935,146 A | 8/1999 | McEwen | |
| 5,951,502 A | 9/1999 | Peeler | |
| 6,051,016 A * | 4/2000 | Mesaros et al. | ............... 606/202 |
| 6,213,939 B1 | 4/2001 | McEwen | |

(Continued)

FOREIGN PATENT DOCUMENTS

WO    197747    12/2001

OTHER PUBLICATIONS

AORN Standards, Recommended Practices, and Guidelines, 2007 Edition; Recommended Practices for the Use of the Pneumatic Tourniquet in the Perioperative Practice Setting; circa Jan. 1, 2007; pp. 617-629.

(Continued)

*Primary Examiner* — Gregory J. Redmann
(74) *Attorney, Agent, or Firm* — Hancock Hughey LLP

(57) ABSTRACT

Apparatus for estimating a magnitude of leakage from a surgical tourniquet system while pressure in a cuff of the system is regulated near a reference pressure.

8 Claims, 3 Drawing Sheets

U.S. PATENT DOCUMENTS

| | | |
|---|---|---|
| 6,371,937 B1 * | 4/2002 | McPhee .................. 604/118 |
| 6,475,228 B1 | 11/2002 | Mesaros |
| 6,589,268 B1 | 7/2003 | McEwen |
| 6,605,103 B2 | 8/2003 | Hovanes |
| 6,682,547 B2 | 1/2004 | McEwen |
| 7,331,977 B2 | 2/2008 | McEwen |
| 7,479,154 B2 | 1/2009 | McEwen |
| 2003/0036771 A1 | 2/2003 | McEwen |
| 2003/0126912 A1 | 7/2003 | Cook |
| 2003/0167070 A1 | 9/2003 | McEwen |
| 2003/0236548 A1 | 12/2003 | Hovanes |
| 2004/0147956 A1 | 7/2004 | Hovanes |
| 2006/0224181 A1 | 10/2006 | McEwen |
| 2006/0253150 A1 | 11/2006 | McEwen |
| 2006/0287672 A1 | 12/2006 | McEwen |
| 2007/0032818 A1 | 2/2007 | McEwen |
| 2007/0032819 A1 | 2/2007 | McEwen |
| 2007/0255310 A1 | 11/2007 | Hovanes |
| 2008/0262533 A1 | 10/2008 | McEwen |
| 2010/0211096 A1 | 8/2010 | McEwen |

OTHER PUBLICATIONS

International Search Report and Written Opinion: related application No. PCT/CA2010/000176; May 18, 2010; 13 pages.

* cited by examiner

APPARATUS AND METHOD FOR ESTIMATING LEAKAGE IN A SURGICAL TOURNIQUET SYSTEM

FIELD OF THE INVENTION

This invention pertains to pneumatic tourniquet systems commonly used for stopping the flow of arterial blood into a portion of a surgical patient's limb to facilitate the performance of a surgical procedure and for facilitating intravenous regional anesthesia.

BACKGROUND OF THE INVENTION

Surgical tourniquet systems are commonly used to stop the flow of arterial blood into a portion of a patient's limb, thus creating a clear, dry surgical field that facilitates the performance of a surgical procedure and improves outcomes. A typical surgical tourniquet system of the prior art includes a tourniquet cuff for encircling a patient's limb at a desired location, a tourniquet instrument, and flexible pneumatic tubing connecting the cuff to the instrument. In some surgical tourniquet systems of the prior art, the tourniquet cuff includes an inflatable portion, and the inflatable portion of the cuff is connected pneumatically through flexible plastic tubing and one or more connectors to a tourniquet instrument. A typical tourniquet instrument of the prior art includes a pressure regulator to maintain the pressure in the inflatable portion of the cuff, when applied to a patient's limb at a desired location, near a reference pressure that is above a minimum pressure required to stop arterial blood flow past the cuff during a time period suitably long for the performance of a surgical procedure. Many types of such pneumatic surgical tourniquet systems have been described in the prior art, such as those described by McEwen in U.S. Pat. No. 4,469,099, No. 4,479,494, No. 5,439,477 and by McEwen and Jameson in U.S. Pat. No. 5,556,415 and No. 5,855,589.

In surgical tourniquet systems of the prior art, leakage of pressurized gas from the tourniquet cuff, or from pneumatic tubing between the instrument and cuff, or from connectors attaching the tubing to the cuff and instrument may affect safety, performance, and reliability. The 2007 Recommended Practices for the Use of the Pneumatic Tourniquet in the Perioperative Practice Setting (RPs) of the US Association of periOperative Nurses (AORN) recommend that the tourniquet cuff, tubing, and connectors should be kept clean and in good working order. The AORN RPs further recommend, based on published literature, that the tourniquet cuff, tubing, and connectors should be inspected for cracks and leaks because unintentional pressure loss can result from loose tubing connectors, deteriorated tubing, or cuff bladder leaks, and may result in patient injury. At present, such inspections and checking are performed manually and often inconsistently by users, or only after a hazardous incident or patient injury has occurred. As a result, defective and leaking tourniquet cuffs, connectors and tubing may remain in use for long periods of time. Also, users may not be alerted to defects which may be small initially but which may increase to become significant hazards, either slowly or very rapidly, if remedial action is not taken. Unauthorized reprocessing and reuse of cuffs manufactured to be single-use disposable cuffs may introduce leakage hazards if such cuffs are not carefully inspected and checked before each reuse because improper, uncontrolled and unlimited reprocessing may impair the shape and integrity of the pneumatic seals of cuff connectors. Even if disposable tourniquet cuffs are used as single-use products, and if it is assumed that such cuffs are not leaking at time of first use, the tubing and connectors that connect the disposable cuffs to the tourniquet instrument may leak and such leakage may go undetected, allowing the leaking tubing or connectors to remain in use until an obvious patient hazard or injury occurs, and during which time other limitations in tourniquet safety, performance and reliability are produced, as described below.

To alert a user to an extreme loss of tourniquet cuff pressure from leakage, for example as may be caused by a pneumatic disconnection between the cuff and the instrument, some surgical tourniquet systems of the prior art include audio-visual leakage alarms. Unfortunately, such alarms in prior-art systems are typically produced only after there has been a decrease in actual cuff pressure to a level that is well below the reference pressure for a sustained period of time, and thus only after substantial blood flow past the cuff may have occurred. This adversely affects the safety and quality of surgery before the user is alerted to the need for remedial action.

Sustained pneumatic leakage that is not detected by prior-art tourniquet systems is undesirable in surgery and may be hazardous. In the past, undetected pneumatic leakage led users of prior-art systems to set tourniquet pressures at reference levels that were substantially higher than required physiologically to compensate for intra-operative reductions in cuff pressure that users had observed but had not been able to attribute to obvious leakage. However, setting unnecessarily high pressures is hazardous because in the medical literature higher tourniquet pressure levels have been associated with higher probabilities of patient injuries to nerves and soft tissues. More recently, some surgical tourniquet systems of the prior art have attempted to compensate for undetected levels of pneumatic leakage in the design of their pressure regulators. In typical systems, the pressure regulator is designed to maintain cuff pressure within a predetermined pressure range from a reference pressure, and any fluctuations beyond that range are offset by actuation of a pump, reservoir, or valve in an effort to bring the cuff pressure back within the range. If there is pneumatic leakage sufficient to cause the cuff pressure to decrease beyond the predetermined pressure range, actuation of the pressure regulator may bring it back within range, and if not a pressure-regulation alarm is produced. Such systems of the prior art may compensate for significant levels of sustained, undetected leakage without producing any indication of leakage or alarm for the user. As a result of this limitation, defective and leaking tourniquet cuffs, connectors, and tubing may remain in use for long periods of time. Further, sustained leakage may produce an error in the indicated tourniquet cuff pressure in single-port tourniquet systems of the prior-art which estimate cuff pressure by measuring pneumatic pressure within the tourniquet instrument. Also, users are not alerted to defects which may be small initially but which may increase to become significant hazards, either slowly or very rapidly, if remedial action is not taken. For typical surgical tourniquet systems of the prior art three limitations in the performance and reliability of their pressure regulators exist in the presence of undetected pneumatic leakage. First, tourniquet cuff pressure fluctuates unnecessarily as decreases in cuff pressure are offset by the actuations of the pressure regulator. Second, unnecessarily frequent actuation of the pressure regulator reduces the operational life and reliability of its mechanical components, increases the cost of maintaining and replacing those components, and may increase capital costs by necessitating early replacement of the entire tourniquet instrument. Third, operation of prior-art tourniquet systems on battery power is impaired. Typical tourniquet systems of the prior art may be powered either by external AC power or by an internal battery, so that they can continue to operate safely in the event of a sudden interruption of external power, and so that they can operate independently of external AC power for a prolonged period of time, for example during transportation of a patient from a pre-operative room to the operating room, or to facilitate surgery under emergency or battlefield conditions. However, in the presence of sustained leakage pneumatic leakage, the operational time of a tourniquet system when powered by an internal battery for surgery may be substantially reduced due to unnecessary actuations of the pressure regulator. Additionally, the overall life of the internal battery may be significantly reduced, reducing the performance and reliability of the tourniquet system and thereby increasing costs and hazards.

There is a need for a leak detector for surgical tourniquet systems that overcomes the above-described limitations of the prior art. No surgical tourniquet system known in the prior art rapidly detects leakage in the tourniquet cuff, pneumatic tubing, or pneumatic connectors between the cuff and pressure regulator of the tourniquet instrument while cuff pressure is maintained near a reference pressure by the pressure regulator. Further, no system known in the prior art estimates the magnitude of pneumatic leakage while cuff pressure is regulated near the reference pressure. No prior-art system determines the level of hazard to a patient associated with the magnitude of any pneumatic leakage estimated during cuff pressure regulation. Also, no prior-art tourniquet system includes means for communicating with a remote display, printer, alarm or similar apparatus to produce an indication perceptible by a user of the level of hazard associated with any pneumatic leakage detected during cuff pressure regulation.

DETAILED DESCRIPTION OF THE PREFERRED EMBODIMENT

The embodiment illustrated is not intended to be exhaustive or limit the invention to the precise form disclosed. It is chosen and described in order to explain the principles of the invention and its application and practical use, and thereby enable others skilled in the art to utilize the invention.

Figure 1:
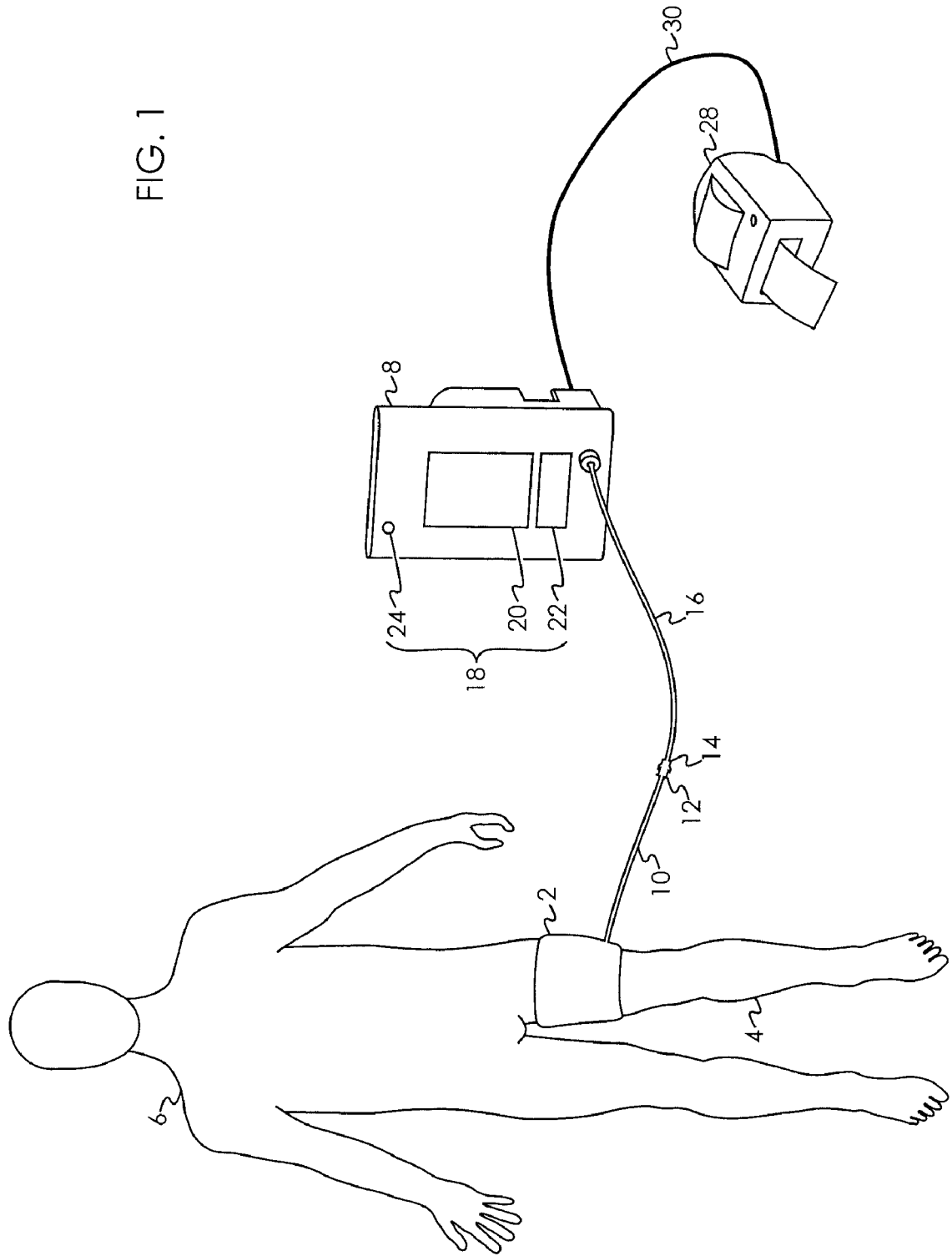
FIG. 1 is a pictorial representation of the preferred embodiment in a surgical application.

FIG. 1 shows an inflatable tourniquet cuff 2 applied to a limb 4 of patient 6 and pneumatically connected to instrument 8. Cuff 2 is supplied with pressurized gas from instrument 8 to occlude the flow of arterial blood in limb 4 past cuff 2. In the preferred embodiment the gas is air, but it will be apparent that other gases or fluids may be used to pressurize cuff 2. A pneumatic passageway to cuff 2 is provided by cuff tubing 10. Cuff tubing 10 is shown to be of sufficient length to allow a pneumatic connection to cuff 2 to be made outside of a sterile surgical field. Cuff tubing 10 is fitted with a male locking connector 12, and mates to form a releasable pneumatic connection with female locking connector 14. Female locking connector 14 is fitted to flexible plastic tubing 16 which connects to instrument 8. Additional connectors may be used to connect tubing 16 to instrument 8 or be otherwise included in the pneumatic passageway between cuff 2 and instrument 8.

Cuff 2 is generally similar in design and construction to the cuffs described by McEwen in U.S. Pat. No. 5,741,295, No. 5,649,954, and by Robinette-Lehman in U.S. Pat. No, 4,635, 635. Cuff 2 may be formed of plastic coated fabric materials that can withstand, and that can be sterilized by techniques normally used to sterilize medical devices to a level of sterility that allows them to be safely used within a sterile surgical field. Cuff 2 may also be formed of materials that can withstand multiple cleaning and disinfection cycles by techniques normally used to clean and disinfect medical devices which are used during surgical procedures. The pneumatic passageway formed by the inflatable portion of cuff 2, the connections made by connectors 12 and 14, and tubing 16 does not normally permit the escape of gas at the pressures supplied by instrument 8. Accidental damage caused by sharp objects, damage during sterilization or cleaning, wear, and manufacturing defects may cause the sustained leakage of gas from cuff 2, connectors 12 and 14 and tubing 16 when cuff 2 is pressurized.

Instrument 8 includes a user interface 18 that comprises a color graphic display panel 20, a keypad 22, and an alarm indicator 24. A similar user interface, employing a monochromatic graphic display panel has been described in U.S. Pat. No. 5,556,415.

Display panel 20 is employed for the selective display of any of the following information: the level of pressure within cuff 2 as measured by instrument 8 (cuff pressure); the pressure level to be maintained in cuff 2 when cuff 2 is pressurized (reference pressure level); alarm reference "limits" or values; alarm and warning messages describing detected alarm events; magnitudes of detected leaks and leakage trends; menus of commands for the operation of instrument 8; and other information and instructions pertinent to the operation of instrument 8. To facilitate a clear and rapid understanding of the information presented to the user of instrument 8, alphanumeric text, graphic symbols, and color are all used to convey information.

Keypad 22 provides a means for the user of instrument 8 to control the operation of instrument 8.

Instrument 8 signals the presence of alarm conditions via alarm indicator 24 and symbols and text messages describing the alarm condition displayed upon display panel 20. Alarm indictor 24 includes a visual indicator in the form of a red lamp and a speaker for generating audio tones. An example of a detected alarm condition that requires the user's attention is the detection of a hazardous leak from cuff 2 or from the tubing and connectors forming the pneumatic passageway between cuff 2 and instrument 8.

It will be appreciated that other types of user interface may be used by the invention, for example keypad 22 could be replaced by a touch screen interface to display panel 20 allowing the user to interact with instrument 8 by touching selected areas of display panel 20; a multi segment LCD or LED display could be selected for display panel 20; or the user interface could be provided by another device in communication with instrument 8.

Instrument 8 maintains a register of events, similar to that described in U.S. Pat. No. 5,911,735, to record events and store the levels of relevant parameters at the time of the event such as cuff pressure, reference pressure level, estimated magnitude of leakage, inflation time, and alarm thresholds. Events that are recorded and stored by event register 26 shown in FIG. 2 include: hazardous leakage from cuff 2 and the connection between cuff 2 and instrument 8; the pressurization of cuff 2; the deflation of cuff 2; adjustments made to the reference pressure level; detected alarm conditions and adjustments made to alarm limits.

Event printer 28 is connected to instrument 8 via interface cable 30. Event printer 28 provides a hard copy printout of the events and the levels of parameters associated with the event as recorded and stored by instrument 8. A record of events may be communicated by instrument 8 to an external operating room information network 32 for subsequent display along with data collected from other instrumentation in the operating room.

In addition to communicating the stored events and the levels of parameters associated with an event to printer 28 and network 32, event register 26 may in response to a request communicate the current levels of operating parameters including cuff pressure, cuff reference pressure, magnitude of leakage, inflation time, and other parameters relevant to the operation of instrument 8 to printer 28 and to network 32.

Figure 2:
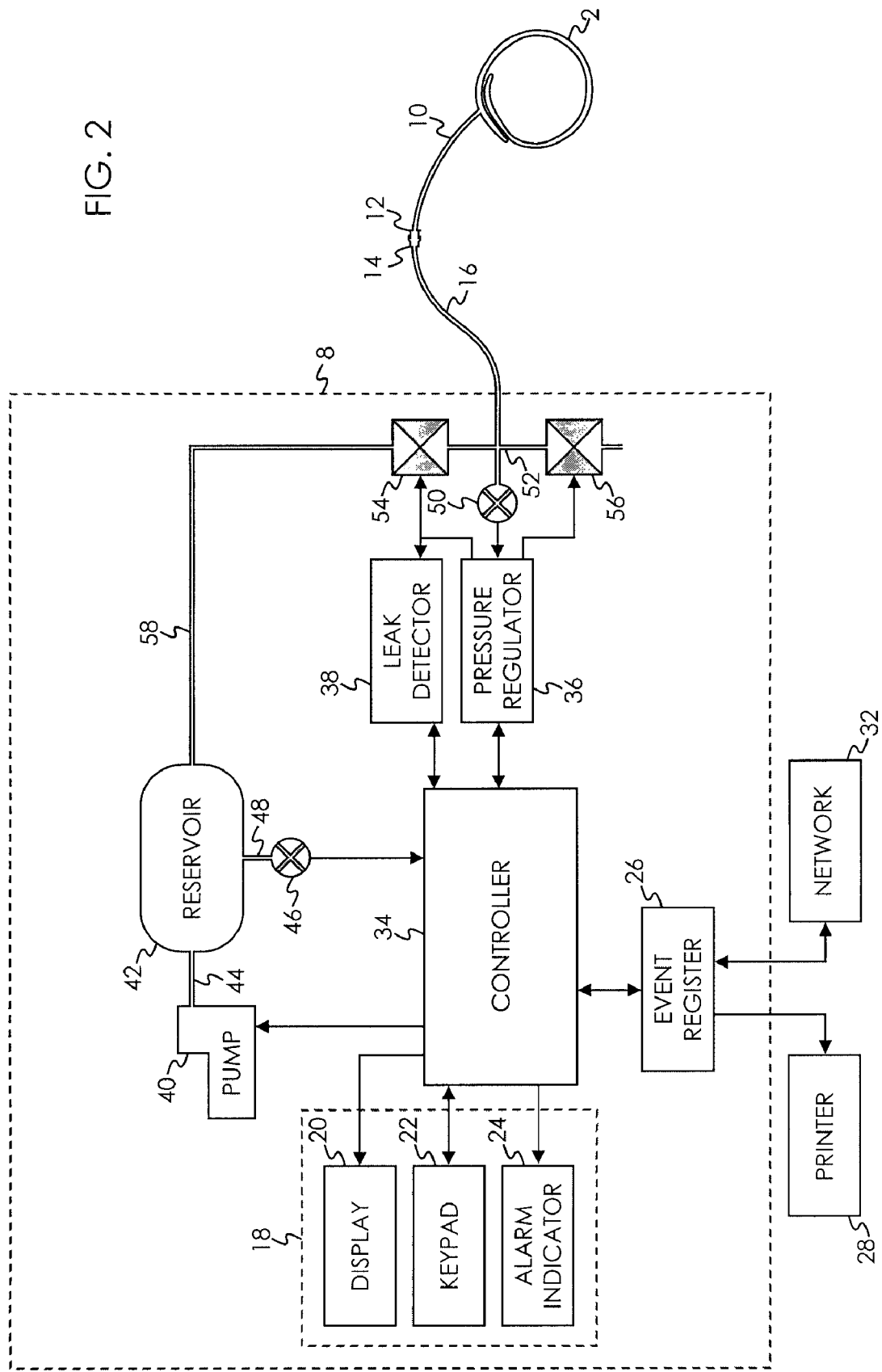
FIG. 2 is a block diagram of the preferred embodiment.

A block diagram of instrument 8 is shown in FIG. 2. Referring to FIG. 2, controller 34 is a microcontroller typical of those known in the art with associated memory, analog, and digital peripheral interface circuitry, and other support components. Controller 34 executes software programs that control the operation of instrument 8 as described below. For clarity, and to enable a better understanding of the principles of the invention, some functions that are performed by controller 34 are described and shown in FIG. 2 as separate functional blocks. These function blocks are pressure regulator 36, leak detector 38 and event register 26.

The assemblage of components for regulating cuff pressure include a source of pressurized gas that is generated by pneumatic pump 40 which is pneumatically connected to reservoir 42 by tubing 44. In response to control signals from controller 34, pump 40 operates to pressurize reservoir 42. Reservoir pressure transducer 46 is pneumatically connected by tubing 48 to reservoir 42 and generates a signal indicative of the pressure within reservoir 42, which is communicated to controller 34. Controller 34 activates pump 40 to maintain the pressure in reservoir 42 near a predetermined level. It will be appreciated that an external source of pressurized gas for the pressurization of cuff 2 could be provided to instrument 8 eliminating the necessity for pump 40 and reservoir 42.

Pressure regulator component 36 receives a cuff pressure signal indicative of the pressure within cuff 2 from pressure transducer 50. Pressure transducer 50 is pneumatically connected to cuff 2 via manifold 52 and the pneumatic passageway formed by tubing 16, connectors 12 and 14, and cuff tubing 10. The cuff pressure signal is communicated to controller 34 and leak detector 38 by pressure regulator 36. As shown if FIG. 2, cuff pressure transducer 50 shares a common pneumatic connection to cuff 2 with pressure increase valve 54 and pressure decrease valve 56. Other configurations of pneumatic connection to cuff 2 may be employed, for example, an additional port may be included in cuff 2 for direct connection to transducer 50, or transducer 50 may be incorporated into cuff 2.

When enabled by controller 34, pressure regulator 36 operates to maintain the pressure in cuff 2 (cuff pressure) near the reference pressure level by selectively actuating pressure increase valve 54 and pressure decrease valve 56. The reference pressure level may be adjusted and set by the user of instrument 8 via user interface 18 and also adjusted and set automatically by controller 34 in response to the physiologic condition of patient 2 as described in the prior art.

Pressure increase valve 54 is an electrically operated normally closed pneumatic valve. The inlet of valve 54 is pneumatically connected via tubing 58 to reservoir 42, the outlet of valve 54 is connected to cuff 2 via the pneumatic passageway formed by manifold 52, tubing 16, connectors 14 and 12, and cuff tubing 10. A pressure increase signal from pressure regulator 36 supplies electrical power for the operation of pressure increase valve 54. When supplied with electrical energy valve 54 opens to allow gas to flow from reservoir 42 to cuff 2, thereby increasing the pressure of gas in the inflatable portion of cuff 2. The amount of electrical power supplied by pressure regulator 36 to valve 54 controls the average rate of gas flow through valve 54. The electrical characteristics of the pressure increase signal are adapted to be appropriate for the operating requirements of valve 54. Valve 54 may be configured as an electrically operated proportional valve wherein the rate of gas flow through valve 54 varies as a function of the electrical current supplied to the valve. Or, valve 54 may be configured as an electrically operated solenoid valve that may be either fully open or fully closed; the average rate of gas flow through the valve may be controlled by pulse width modulating the electrical current supplied to the valve. In the preferred embodiment the level of the pressure increase signal corresponds to a percentage of the maximum flow rate that valve 54 is capable of providing. At level of 0% valve 54 is closed and no gas flows through valve 54, at a level of 100% valve 54 is fully open and the flow rate through the valve is at a maximum.

A pneumatic pump may be used in place of pressure increase valve 54 to directly supply gas to increase the pressure in cuff 2 in response to the pressure increase signal from pressure regulator 36. In this case, the rate at which gas is supplied by the pump to cuff 2 also corresponds to the level of the pressure increase signal, with 0% being no flow from the pump and 100% being the maximum flow rate that the pump is capable of.

Pressure decrease valve 56 is also an electrically operated two position normally closed valve similar to valve 54. The inlet of valve 56 is pneumatically connected to cuff 2 via the pneumatic passageway formed by manifold 52, tubing 16, connectors 14 and 12, and cuff port 10, the outlet of valve 56 is open to atmosphere. A pressure decrease signal from pressure regulator 36 supplies electrical power for the operation of pressure decrease valve 56. Pressure regulator 36 sets the level of the pressure decrease signal to control the opening of valve 56. Pressure decrease valve 56 responds to the control signal from pressure regulator 36 to allow gas to be vented from cuff 2 to atmosphere, thereby decreasing the pressure of gas in cuff 2.

A proportional integral control algorithm is used by pressure regulator 36 to calculate and set the levels of the pressure increase and pressure decrease control signals for valves 54 and 56 necessary to maintain the cuff pressure near the reference pressure level within a predetermined range. It will be appreciated by those skilled in the art that other pressure regulation control algorithms could be employed by pressure regulator 36 to set the levels of pressure increase and pressure decrease control signals for valves 54 and 56.

Manipulation of limb 4 during surgery may cause the tissue volumes beneath cuff 2 to change and result in a transient increase or decrease of pressure within cuff 2 that is not attributable to leakage. Pressure regulator 36 will respond to a difference in pressure between the reference pressure level and the cuff pressure to add or remove gas from cuff 2 by adjusting the level of the control signals for valve 54 and valve 56 thereby increasing or decreasing the gas pressure within cuff 2 and maintaining the cuff pressure near the reference pressure level. When responding to a change in cuff pressure from limb manipulation, the time taken by pressure regulator 36 to restore the cuff pressure to a level near the reference pressure level is typically less than 2 seconds.

If during limb manipulation or at other times pressure regulator 36 can not maintain the cuff pressure within the operating limits of pressure regulator 36, controller 34 will indicate a high or low pressure alarm condition to the user via user interface 18 and event register 26 will record a corresponding alarm event. In the preferred embodiment an alarm will be indicated if the pressure regulator 36 cannot maintain the cuff pressure with a predetermined regulation limit of plus or minus 15 mmHg of the reference pressure level. It will be appreciated that other regulation limits may be selected and that they need not be symmetrical around the reference pressure level.

To indicate to a user of instrument 8 the magnitude of any leakage of gas from cuff 2 and the pneumatic connection between cuff 2 and instrument 8 during the time when pressure regulator 36 is operating to maintain the cuff pressure near the reference pressure level, the preferred embodiment includes leak detector 38 for estimating a magnitude of leakage.

Figure 3:
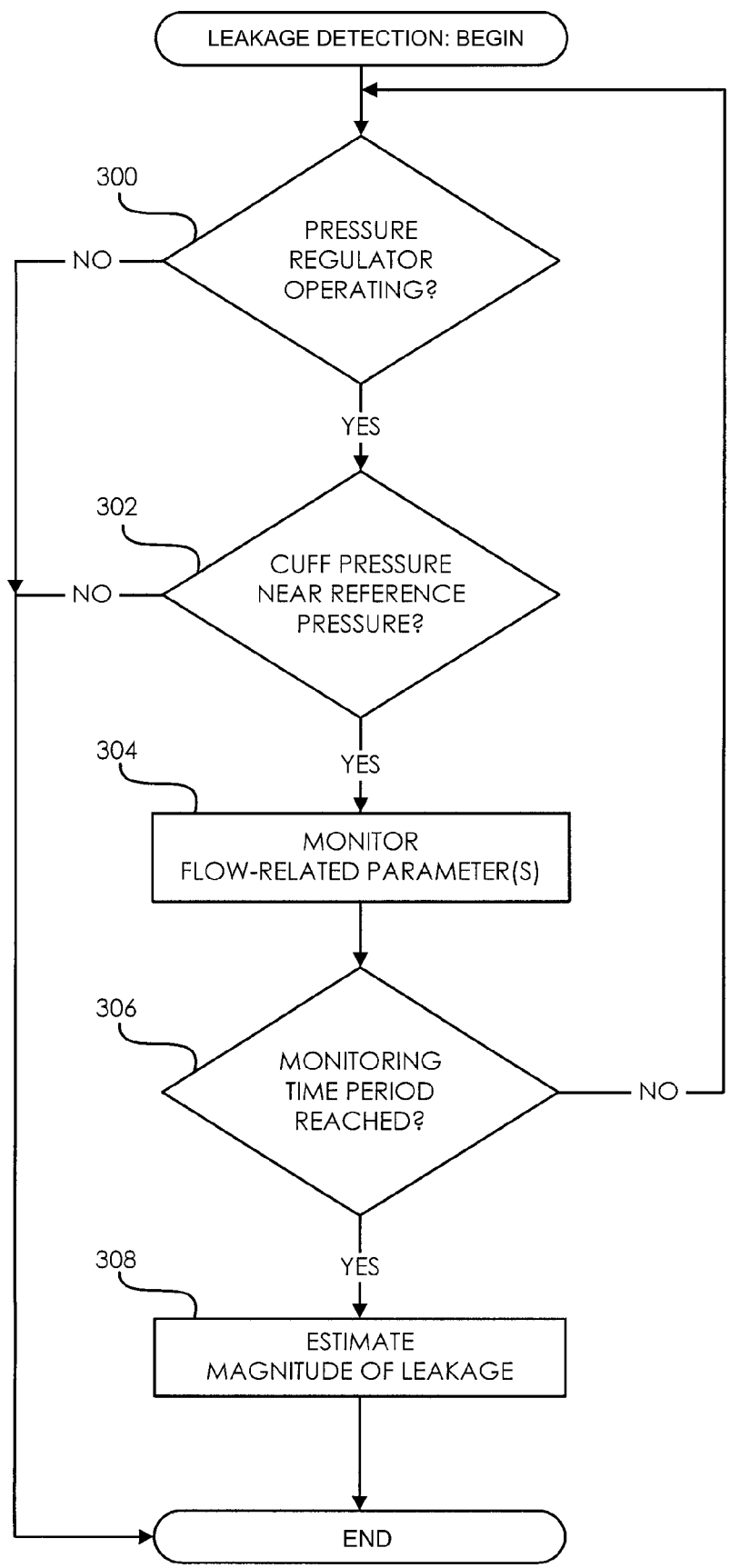
FIG. 3 is a flow chart showing the sequence of operation of the leak detector.

Referring to FIG. 3, when pressure regulator 36 is operating (300) and the cuff pressure is within the regulation limits of pressure regulator 36 (302), leak detector 38 monitors a parameter of operation of pressure regulator 36 that is indicative of the rate of gas flow into cuff 2 (304). The parameter is monitored for a period of time (306) after which an estimate of the magnitude of leakage is produced (308) by leak detector 38.

Any leakage of gas from cuff 2 and the connection between cuff 2 and instrument 8 will cause a reduction in cuff pressure. Pressure regulator 36 will act to maintain the cuff pressure at a level near the reference pressure level by actuating pressure increase valve 54 to replenish the gas lost due to the leakage. The rate at which pressure regulator 36 must replenish gas lost due to leakage in order to maintain the cuff pressure near the reference pressure level is proportional to the magnitude of leakage from the system. As noted above, the rate at which gas flows through pressure increase valve 54 is a function of the level of the pressure increase signal.

A parameter of operation of pressure regulator 36 that is indicative of the rate of gas flow into cuff 2 that is monitored by leakage detector 38 is the level of the pressure increase signal for valve 54. Other parameters of operation of pressure regulator 36 indicative of the rate of gas flow into cuff 2 may also be monitored by leak detector 38, such as the amount by which the reference pressure level exceeds the cuff pressure. Because pressure regulator 36 operates to maintain the cuff pressure near the reference level, the amount by which reference pressure exceeds the cuff pressure is an indication of the gas flow required to maintain the cuff pressure near the reference pressure level.

It will be appreciated that leak detector 38 could be configured to monitor gas flow into cuff 2 directly by the addition of one or more gas flow meters to the pneumatic system; this however, would add significant cost and complexity to the system.

Leak detector 38 estimates the magnitude of leakage by: monitoring the level of the pressure increase signal during a monitoring time period; and then estimating the magnitude of leakage as a function of the level of the pressure increase control signal throughout the monitoring time period. The magnitude of leakage estimated by leak detector 38 is proportional to the average flow rate through pressure increase valve 54 over the monitoring time period and is expressed a percentage of the maximum rate of flow of gas that instrument 8 is capable of providing to cuff 2 while maintaining the cuff pressure near the reference pressure level. The magnitude of leakage estimated by leakage detector 38 is indicated to the user via user interface 18.

To differentiate between the transient activation of pressurizing valve 54 caused by pressure regulator 36 compensating for cuff movement and the sustained activation of valve 54 over time caused by a leak, leak detector 38 monitors the level of the pressure increase signal over a monitoring time period that is substantially greater than the transient response time of pressure regulator. In the preferred embodiment the monitoring time period is 20 seconds. It will be appreciated that other predetermined time periods could be selected and that a time period could be automatically selected by controller 34.

To reduce the monitoring time period and improve the accuracy of the magnitude of leakage estimated by leak detector 38, leak detector 38 may be configured to monitor additional parameters of operation of pressure regulator 36 during the monitoring time period. For example, leak detector 36 may be configured to also monitor the pressure decrease signal produced by pressure regulator 36 thereby improving the estimate of leakage magnitude by accounting for gas vented from the system due to regulator 36 responding to increases in cuff pressure caused by manipulation of the limb 4.

Controller 34 compares the estimated magnitude of leakage produced by leakage detector 38 with predetermined thresholds in order to rank the magnitude of leakage and to indicate the degree of hazard to patient 6 from the possibility of arterial blood flowing past cuff 2. An estimated magnitude of leakage of 40% or more is indicated as a high hazard leak. A high hazard leak represents a high probability that pressure regulator 36 may not be able to continue to maintain the cuff pressure near the reference pressure level and that the pressure in cuff 2 may fall to a level that allows arterial blood to flow past cuff 2. A high hazard leak requires the immediate attention of the user to mitigate the leakage and is indicated by the activation of alarm indicator 24 and messages shown on display panel 20. Event register 26 also records the detection of a high hazard leak rate event for later printout by printer 28 and communication to network 32 for subsequent display.

An estimated magnitude of leakage of 25% or more and less than 40% is indicated as a moderate hazard leak by controller 34. A moderate hazard leak represents a lesser probability that pressure regulator 36 will be unable to maintain the pressure in the cuff near the reference pressure. Moderate hazard leaks may not require the user's immediate attention but do require future action to repair or replace cuff 2 and the pneumatic connection between cuff 2 and instrument 8. A moderate hazard leak is indicated by warning messages shown on display panel 20. Event register 26 also records the detection of a moderate hazard leak event for later printout by printer 28 and communication to network 32 for subsequent display.

An estimated magnitude of leakage of 10% or more and less than 25% is indicated as a low hazard leak. A low hazard leak represents a leak with a low probability of potential hazard to the patient, and is however indicative of a potential problem with cuff 2 and the pneumatic connection between cuff 2 and instrument 8 that should be investigated further by the user. A low hazard leak is indicated by warning messages shown on display panel 20 at the end of the surgical procedure when cuff 2 is deflated. Event register 26 also records the detection of a low hazard leak event for later printout by printer 28 and communication to network 32 for subsequent display.

To alert the user to a leak from cuff 2 and the passageway between cuff 2 and instrument 8 that may be increasing in magnitude over time, controller 34 operates to detect trends in leakage magnitude. Controller 34 stores in memory the leakage magnitude estimated by leak detector 38 at predetermined time intervals of 1 minute. Each time controller 34 stores a leakage magnitude in memory it computes a leakage trend value from the difference between the recent leakage magnitude and the previously stored leakage magnitude. The leakage trend value is displayed via user interface 18. If leakage trend value exceeds a predetermined hazardous trend threshold limit, controller 34 alerts the user via user interface 18 that the magnitude of leakage is increasing. This may indicate that a high magnitude leak may soon develop and that mitigating action should be taken immediately. Event register 26 also records an event indicating that the magnitude of leakage has increased over time. In the preferred embodiment, the trend threshold limit is a predetermined increase in leakage magnitude of more than 10% during a 1-minute interval. It will be appreciated that other predetermined time intervals and threshold limits may be selected.

We claim:

1. A method of estimating the magnitude of gas leakage from a surgical tourniquet cuff during an operation time period when the cuff is applied to a patient's limb and connected to a controllable pressure source of gas and when the cuff is pressurized with the gas to be within a reference pressure range suitable for occluding blood flow through the limb, the method comprising the steps of:
    configuring the pressure source to be responsive to an applied electrical signal for directing gas to flow to the cuff at a flow rate corresponding to the electrical current level of the applied electrical signal;
    correlating the current levels of the electrical signal applied to the pressure source with the corresponding gas flow rates to the cuff and saving that correlated information;
    monitoring, during the operation time period, the current levels of the electrical signal applied to the pressure source;
    using the correlated information for calculating the gas flow rate to the cuff during the operation time period; and
    using the calculated gas flow rate for estimating a magnitude of gas leakage from the cuff.

2. The method of claim 1 including the step of accounting for a flow of gas intentionally vented from the cuff.

3. The method of claim 1 including the step of determining the trend in the magnitude of leakage by comparing two estimates of the magnitude of leakage.

4. The method of claim 1 including the steps of ranking the estimated magnitude of leakage and providing to a user an indication corresponding to that ranking 5. The method of claim 1 wherein the monitoring step includes monitoring the current levels of the electrical signal for a monitoring period that is greater than about two seconds.

6. The method of claim 1 wherein the monitoring step further comprises monitoring the current levels for a monitoring time period that is substantially greater than the time required for restoring the level of pressure in the cuff to be within the reference pressure range in response to instances when the cuff pressure moves out of that range as a result of a transient event that is not attributable to leakage.

7. The method of claim 1 including the step of:
    storing a value indicative of the estimate of the magnitude of leakage;
    communicating the stored value to a location remote from the cuff; and
    presenting, subsequent to the operation time period, the stored value in a form perceptible by a user.

8. The method of claim 1 including the step of producing a leakage warning indication that is perceptible by a user if the estimate of the magnitude of leakage is greater than a predetermined hazardous level of leakage.

* * * * *